United States Patent
Bergeron et al.

(10) Patent No.: US 7,906,322 B2
(45) Date of Patent: Mar. 15, 2011

(54) METHOD AND APPARATUS FOR INDUCING CONTROLLED MECHANICAL CONSTRAINTS IN A TISSUE CONSTRUCT

(75) Inventors: François Bergeron, Sainte-Foy (CA); Lucie Germain, St-Augustin (CA); François Auger, Sillery (CA)

(73) Assignee: Organogenesis, Inc., Canton, MA (US)

( * ) Notice: Subject to any disclaimer, the term of this patent is extended or adjusted under 35 U.S.C. 154(b) by 1428 days.

(21) Appl. No.: 10/866,708

(22) Filed: Jun. 15, 2004

(65) Prior Publication Data

US 2005/0019897 A1     Jan. 27, 2005

(51) Int. Cl.
*C12M 1/00*     (2006.01)
*C12M 3/00*     (2006.01)

(52) U.S. Cl. .................. 435/289.1; 435/284.1; 435/366; 73/829; 73/858; 73/831; 73/836

(58) Field of Classification Search ............... 435/289.1, 435/284.1, 366; 73/829, 858, 831, 836; 623/912, 623/901, 920; 100/86; 242/157.1, 410, 615
See application file for complete search history.

(56) References Cited

U.S. PATENT DOCUMENTS

| | | | | |
|---|---|---|---|---|
| 4,852,230 A | * | 8/1989 | Yu | 29/898.07 |
| 5,618,718 A | * | 4/1997 | Auger et al. | 435/366 |
| 5,928,945 A | | 7/1999 | Dunkelman et al. | |
| 6,107,081 A | * | 8/2000 | Feeback et al. | 435/284.1 |
| 6,503,273 B1 | * | 1/2003 | McAllister et al. | 623/1.41 |

OTHER PUBLICATIONS

Sadoshima, J-I et al: "Molecular Characterization of the Stretch-Induced Adaptation of Cultured Cardiac Cells An In-Vitro Model of Load-Induced Cardiac Hypertrophy" Journal of Biological Chemistry, vol. 267, No. 15, 1992 pp. 10551-10560.
"Tytron™ 250 Microforce Testing System" 2001, MTS Systems Corporation, US, Retrieved from Internet.

* cited by examiner

*Primary Examiner* — William H Beisner
*Assistant Examiner* — Danielle Henkel
(74) *Attorney, Agent, or Firm* — Edward J. Adamson; Ravi Dipali

(57) ABSTRACT

A method and a device (10) for reorganizing the fibers of a matrix in a living tissue sheet (S) by inducing controlled mechanical constraints in the living tissue (S) sheet thus causing the fibers of the matrix to be aligned parallel to the strain orientation. The sheet (S) is held in a stretched state until the fibers set in place.

10 Claims, 3 Drawing Sheets

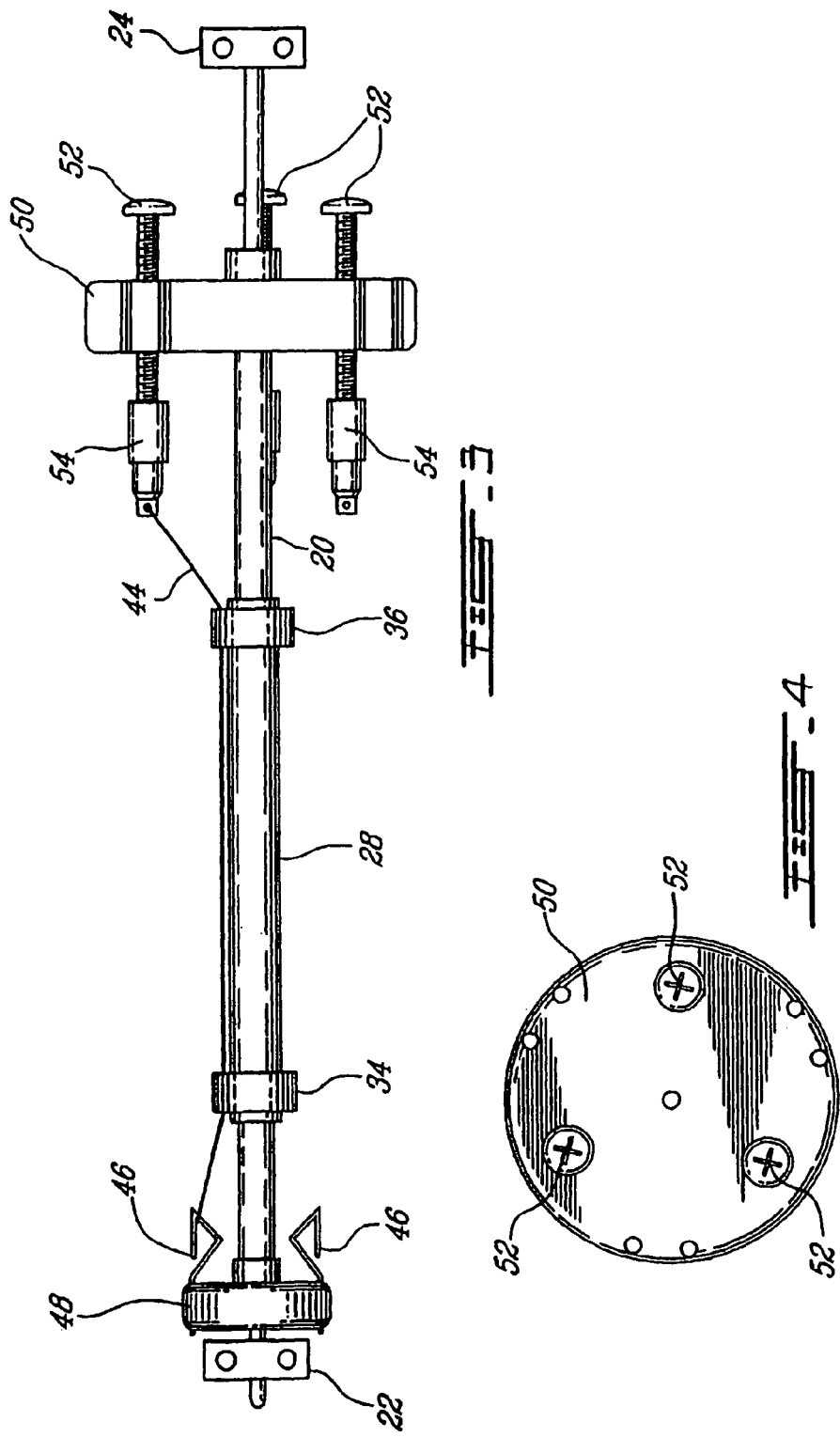

METHOD AND APPARATUS FOR INDUCING CONTROLLED MECHANICAL CONSTRAINTS IN A TISSUE CONSTRUCT

BACKGROUND OF THE INVENTION

1. Field of the Invention

The present invention relates generally to the field of tissue engineering and, more particularly, to a method and an apparatus for use in the production of tissue equivalents from sheets of biomaterial containing live cells.

2. Description of the Prior Art

It is well known by those skilled in the art that mesenchymal cells can be incorporated into reconstructed sheets of tissue. The matrix surrounding the cells in the sheet can be formed either from cell-synthesized extracellular matrix molecules, exogenously added molecules or a mixture of both. These living tissue sheets can be used as the building material to assemble complex tissue equivalents.

The physical properties of such sheets are greatly influenced by the distribution of the fibers composing the matrix surrounding the cells. There is thus a need to find a way of controlling the orientation of the matrix fibers in order to obtain living tissue sheets with improved mechanical and biochemical properties.

SUMMARY OF THE INVENTION

It is therefore an aim of the present invention to provide a device for causing the matrix fibers in a living tissue sheet to be aligned along a predetermined direction.

It is also an aim of the present invention to provide a method of setting the orientation of matrix fibers in a living tissue sheet.

Living mesenchymal cells have the ability to rearrange the matrix fibers, and respond to a mechanical strain by aligning the fibers parallel to the strain orientation. Therefore, in order to obtain a proper alignment of fibers and the resulting mechanical properties of the tissue equivalent, one has to induce a controlled amount of mechanical strain in the assembly.

Therefore, in accordance with the present invention, there is provided a device for causing the matrix fibers in a living tissue sheet to be oriented in a desired direction, the device comprising a take-up unit for receiving and maintaining the living tissue sheet under tension, a tensor for inducing a controlled mechanical strain in the sheet along a predetermined direction while the sheet is being dispensed to the take-up unit, the controlled mechanical strain causing the matrix fibers in the sheet to be aligned parallel to the predetermined direction.

In accordance with a further general aspect of the present invention, there is provided a device for causing the matrix fibers in a living tissue sheet to be oriented in a desired direction, the device comprising at least two holders adapted to hold the living tissue sheet in a stretched state during a matrix reorganization process, said holders inducing a controlled amount of mechanical constraint in the living tissue along a predetermined direction so as to cause the matrix fibers of the living tissue sheet to be aligned parallel to said predetermined direction.

In accordance with a further general aspect of the present invention, the device is made of a material compatible for cell culture and provides for a sterile assembly of living tissue sheets with control on mechanical strain orientation and intensity.

In accordance with a further general aspect of the present invention, there is provided a method of setting the distribution of the matrix fibers in a living tissue sheet, comprising the steps of: a) engaging the living tissue sheet with a strain controlled device, and b) inducing a controlled mechanical strain in the sheet over a period of time sufficient to cause the matrix fibers to set in place with the fibers generally aligned parallel with a strain orientation.

In accordance with a further general aspect of the present invention, there is provided a method of reorganizing the fibers of a matrix in a living tissue sheet, comprising the steps of: a) attaching a first end portion of the living tissue sheet on a rotatable take-up support, b) engaging a second end portion of the living tissue sheet opposite said first end portion thereof with a strain control device, c) winding the sheet onto the rotatable take-up support against a resisting force offered by the strain control device so as to induce a mechanically controlled amount of strain in the sheet while the same is being wound on the take-up support, and d) holding the sheet under tension on the take-up support over a period of time sufficient to cause the matrix fibers to set in place with the fibers aligned generally parallel to a line of action of said resisting force.

BRIEF DESCRIPTION OF THE DRAWINGS

Having thus generally described the nature of the invention, reference will now be made to the accompanying drawings, showing by way of illustration a preferred embodiment thereof, and in which:

FIG. 3 is a top plan view of the take-up unit in accordance with a third embodiment of the present invention; and FIG. 4 is an end view of the take-up unit shown in FIG. 3.

DESCRIPTION OF THE PREFERRED EMBODIMENTS

Figure 1:
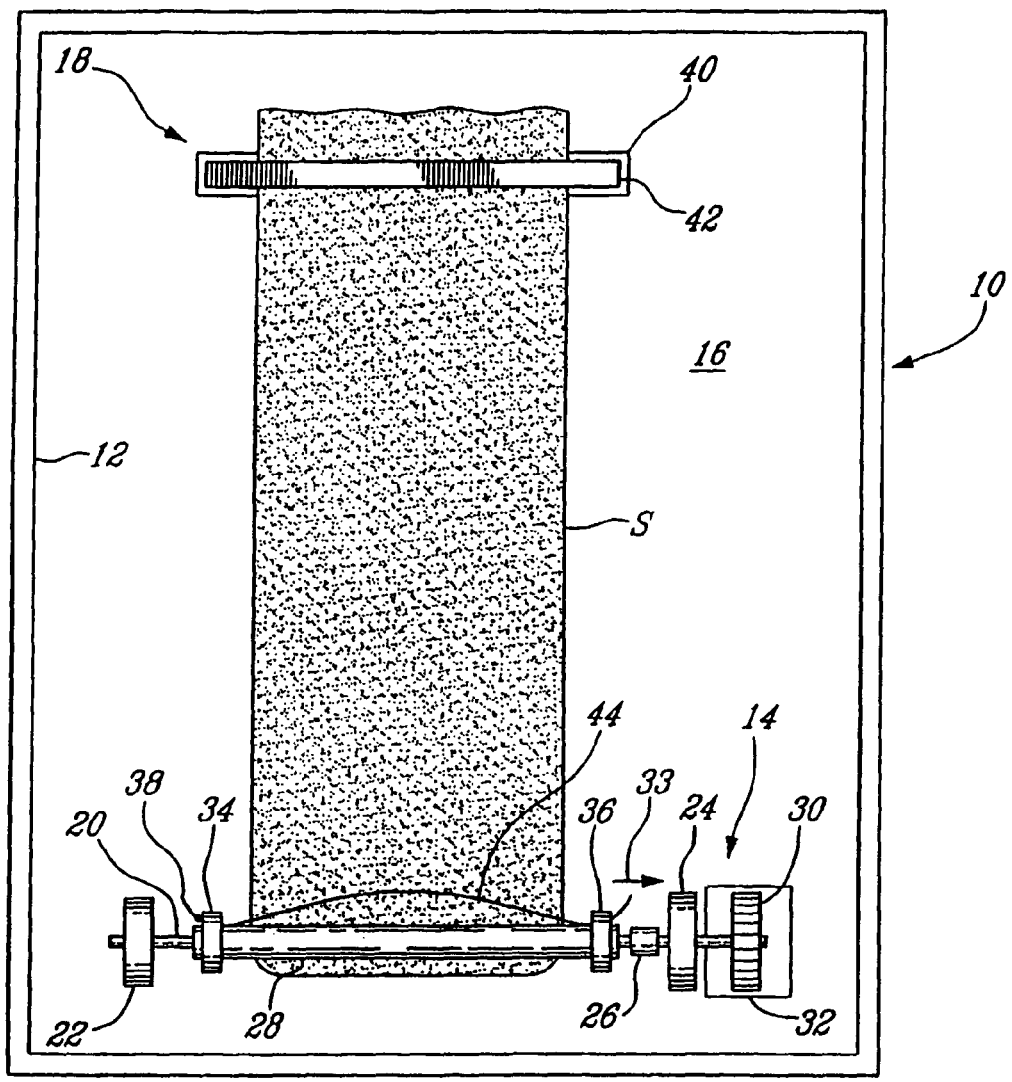
FIG. 1 is a schematic top plan view of a device for inducing controlled mechanical strain in a sheet of living tissue in accordance with a preferred embodiment of the present invention.

Mesenchymal cells like fibroblasts and smooth muscle cells (SMC) express contractile proteins that allow them to induce tensions in the collagen fibers around them. They also express a wide range of extracellular matrix proteins as well as a large variety of matrix-degrading enzymes, which makes the extracellular matrix a very dynamic environment when populated by living cells. Molecular sensors for which the mechanism of action is still poorly understood, will react to the mechanical stimuli applied on the extracellular matrix fibers and result in the orientation of the cells parallel to the direction of the force vector applied. Therefore, in a matrix submitted to anisotropic forces (equal in each direction), the cell orientation will be random and the matrix will contract equally in all directions. On the other hand, when a vectorized mechanical force (static or pulsative) is induced in the matrix fibers, the cells will become oriented parallel to the line of action of this force and will pull on the fibers accordingly. The resulting alignment of the matrix fibers improves the mechanical resistance of the construct.

It is known that cells of mesenchymal origin grow as a multilayer of cells intertwined in an extracellular matrix (e.g. collagen) synthesized by the cells themselves. When these cells are cultured in the presence of ascorbic acid, they reach confluence faster and the proportion of the collagenous component of the above-mentioned cultures increases drastically.

If these cells are maintained in culture several days post confluence cells and matrix will detach as a whole from the culture substratum, thus, creating a sheet of living cells in a collagenous matrix of enogenous origin.

As will be seen hereinafter, the induction of mechanical constraints in such a sheet of living cells can advantageously be used to obtain a tissue equivalent having specific mechanical properties in a given direction. This can be done with spatially fixed anchors that will hold the tissue under tension during the matrix reorganization process. It is important to control the amount of stretch that is induced in the living tissue sheets between the anchors. Living tissue sheets require delicate handling and the controlled amount of strain must be maintained until it is securely bound to the anchors.

Generally, this can be accomplished through the use of a device comprising a support member, which can be a take-up cylinder, a take-up sphere, or any other structure that is required to give the construct its desired shape. The support member is fitted with anchors that will efficiently hold the tissue sheet (i.e. the construct) without damaging it. The support member can be mounted to rotate in many directions, depending on the desired orientation of the cell and fibers around the shape thereof. The support member can be made of any material that is suitable for its purpose, e.g. synthetic or biologic polymer, metal or living tissue. A strain control unit is provided to induce a control amount of strain in the sheet while the same is being held by the support member. The strain control unit is provided with appropriate anchors for holding the tissue sheet during the controlled-strain assembly. Strain can be controlled by any appropriate method, such as by friction, viscosity or electronically.

Now referring to FIG. 1, a device 10 for forming, from a planar living tissue sheet S, a tubular tissue construct having a predetermined matrix fiber orientation will be described. This is a particular example of a process in which the living tissue sheet will benefit from a controlled mechanical strain. In the case of a tubular construct, two main force vectors are applied to the fibers of the matrix. These are the axial and the tangential forces. Thus, when rolled or wound on a solid winding mandrel or cylinder, the fate of the tissue construct will depend on the balance between these two forces. If the axial force is greater than the tangential one, the cells will align axially and exert their traction in this direction. Since there is no physical support on the mandrel to counteract this traction, it will result in the shortening of the tube length, which will proceed until it becomes very short. On the other hand, if the tangential force is greater than the longitudinal one after the sheet has been rolled onto the mandrel, the cells will contract around the mandrel. Since the mandrel is made of solid material, this traction will be counteracted and all the cells will become circumferentially oriented, with no possibility of further contraction of the extracellular matrix. Therefore, proper balance has to be achieved between the two forces when assembling the sheet around the mandrel. These forces must be artificially maintained until the fusion or setting of the cellular matrix between the sheets is sufficient to maintain it by itself.

As shown in FIG. 1, the device 10 generally comprises a top-open container 12 adapted to contain a culture medium, such as a cell culture medium supplemented with ascorbic acid, a take-up unit 14 mounted within the container 12 on a flat bottom surface 16 thereof, and a strain control unit 18 mounted on the bottom surface 16 at an axially spaced-apart location from the take-up unit 14.

The container 12 can be made of various inert and impermeable materials. However, it is usually made of acrylic. It is preferable to use a material that can be readily cleaned and sterilized.

The take-up unit 14 comprises a stainless steel axle 20 journaled to a pair of acrylic bushings 22 and 24 mounted to the bottom surface 16 of the container 12. The bushing 22 is removably secured to the bottom surface 16 and the axle 20 has silicon flexible joint 26, allowing a mandrel 28 to be slid axially on the axle 20 by disengaging the bushing 22 from the axle 20 and by then bending the axle 20 upwards at the flexible joint 26. The mandrel 28 is keyed or otherwise secured to axle 20 to ensure joint rotation of the axle 20 and the mandrel 28. A geared wheel 30 is mounted at one end of the axle 20. The geared wheel 30 is fitted in a groove 32 defined in the bottom surface 16 of the container 12 for allowing the axle 20 and, thus, the mandrel 28 to be manually or power driven in rotation about their longitudinal axes. A one-way clutch mechanism (not shown) is provided to allow the axle 20 and the mandrel 28 to be rotated in one direction only. The mandrel 28 is equipped with a thread 44 which is adapted to be set longitudinally to the external surface of the mandrel 28. To ensure that the thread 44 is closely laid to the surface of the mandrel 28, tension is provided by two elastic collars 34 and 36 mounted at opposed end of the mandrel 28. A knot 38 is formed at one end of the thread 44 to prevent the same from being pulled out of engagement from the collars 34 and 36. The collars 34 and 36 are preferably made of a silicon elastomer.

Figure 2:
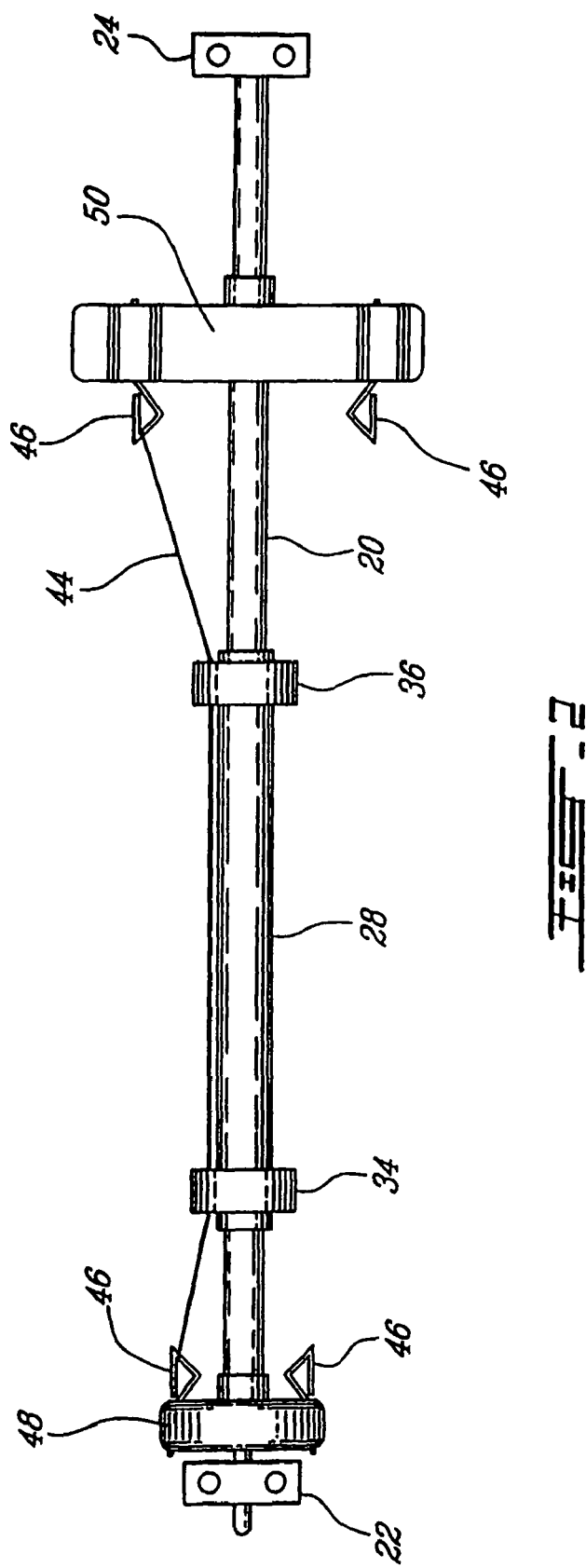
FIG. 2 is a top plan view of a take-up unit in accordance with a second embodiment of the present invention.

Alternatively, as shown in FIG. 2, the thread could be maintained under tension along the mandrel 28 by means of a pair of hooks 46 projecting laterally from a pair of spaced-apart discs 48 and 50 mounted on the axle 20 for rotation therewith. One end of the thread 44 is engaged with one of the hooks 46 on the disc 48 and the other end thereof is engaged with one of the hooks 46 on the second disc 50. The hooks 46 on each disc are circumferentially distributed on the inner facing surface thereof. Other threads can be provided and engaged with the other pairs of hooks 46 to further secure the sheet of tissue in a rolled state on the mandrel at a selected number of turns thereon.

The tension on the thread 44 can be adjusted by moving the elastic collars 34 and 36 or, alternatively, through the operation of adjustable screws 52, as shown in FIG. 3. According to this further embodiment of the present invention, the hooks 46 on the disc 50 are replaced by a series of circumferentially distributed set screws 52 threadably engaged with the disc 50. Adaptors 54 are provided at the distal end of each screw 52 for attachment with the thread 44. The screws 52 permit to repeatedly adjust the tension at the same level for different experiments. The screws 52 also provide for a gradual adjustment of the tension in the thread 44.

To roll the living tissue sheet on the mandrel 28, one end of the sheet S is placed between the mandrel 28 and the thread 44. The thread 44 is pulled as indicated by arrow 33 in order to squeeze the end of the sheet S between the thread 44 and the outer surface of the mandrel 28.

The opposed end portion of the sheet S is engaged with the strain control unit 18. According to the first illustrated embodiment of the present invention, the strain control unit 18 comprises a flat plastic magnet 40 secured to the bottom surface 16 of the container 12 and an overlying metal weight 42. The sheet S is passed between the metal weight 42 and the magnet 40. The metal weight 42 is frictionally engaged with the sheet so as to offer a resistance to the winding of the sheet about the mandrel 28 when the geared wheel 30 is manually operated to drive the mandrel 28 in rotation. The frictional force applied on the sheet by the weight 42 induces a mechanical strain in the sheet S as the same is being wound on the mandrel 28. In this way, a control amount of mechanical strain can be induced in the sheet S while the same is being shaped in a tubular form about the mandrel 28.

When the winding operation is completed and the sheet is still maintained under tension, the so formed roll of living tissue is secured with a fastener, such as a 1/16 inch silicone thread (not shown) held by two removable nylon hose clamps (not shown) placed inside the silicon collars 34 and 36. It is important to secure the roll against unrolling movement while the sheet S is still maintained under tension by the strain control unit 18. Once the roll is secured with the appropriate tension in the sheet S, the remaining part of the sheet S is cut with a cutting tool, such as a scalpel blade. The mandrel 28 can then be removed from the axle 20.

Thereafter, the tubular living tissue can be cultured for several weeks to allow further maturation of the tissue. After 1-2 days, the roll of sheet will adhere to itself relatively firmly and will stay in its tubular form. The fibers of the extracellular matrix of the sheet S will set in place along a direction parallel to the direction of the strain induced in the sheet S by the strain control unit 18, thereby providing a tubular tissue with improved mechanical and biochemical properties. This process can be repeated as required to obtain a multiple sheet assembly with specific fiber and cell orientations.

It is understood that all parts of the device 10 are previously sterilized by either autoclave or ethylene oxide before the winding process. The entire process is done under a sterile culture hood with sterile surgical gloves.

The bottom surface 16 can alternatively be made of a magnetic material. In this case the magnet 40 is no longer necessary and the resistance needed to induce the mechanical strain is built up by the metal weight 42 and the bottom surface 16. Also the bottom surface 16 could be made out of metal or be composed of a layer of metal. Then, the weight 42 would be made out of a magnetic material.

The take-up unit 14 could be connected to a motor thus making it possible to roll at a constant speed.

Alternatively to placing the living tissue sheet on the bottom surface 16, the living tissue sheet could be placed on a plate mounted for sliding movement between a pair of lateral guides on the bottom surface 16 (plate not shown). The guides together with the sliding plate would provide for improved control on the movement of the living tissue sheet.

The tensor or strain control unit 18 could be connected by threads to a tension regulating unit that allows defined adjustment of the tension that can include measurement and control of the applied tension in order to enhance repeatability.

The invention claimed is:

1. A device for causing the matrix fibers in a living tissue sheet to be oriented in a desired direction, the device comprising at least two holders adapted to hold the living tissue sheet in a stretched state during a matrix reorganization process, wherein one of said holders comprises a take-up unit adapted to impart a desired form to the living tissue sheet, said take-up unit includes a winding mandrel keyed to an axle, wherein a thread extends along the winding mandrel, said thread is maintained under tension via two hooks associated with the axle, said thread is further selectively tensioned via a pair of moveable collars that are moveable along the length of the mandrel, said holders inducing a controlled amount of mechanical constraint in the living tissue along a predetermined direction so as to cause the cells and the matrix fibers of the living tissue sheet to be aligned parallel to said predetermined direction.

2. A device as defined in claim 1, wherein the other one of said holders comprises a tensor for inducing a controlled mechanical strain in the sheet while the same is being dispensed to the take-up unit.

3. A device as defined in claim 2, wherein said tensor is provided with a sheet engaging portion adapted to frictionally engage the living tissue sheet so as to apply a force of resistance on the sheet while the same is being dispensed to the take-up unit.

4. A device as defined in claim 1, wherein said take-up unit comprises a winding member rotatably mounted in a culture container containing a culture medium.

5. A device as defined in claim 2, wherein said tensor includes first and second members adapted to receive therebetween the living tissue sheet, the first and second members frictionally engaging the sheet to offer a resistance to a winding action of the take-up unit on the sheet.

6. A device as defined in claim 5, wherein said first member includes a magnet, and wherein said second member includes a metal weight.

7. A device as defined in claim 1, wherein said axle is supported at opposed end portions thereof by a pair of bushings, and wherein a flexible joint is coupled to said axle between said bushings for facilitating loading of said mandrel on said axle.

8. A device as defined in claim 1, wherein a geared wheel is coupled to said axle for allowing a torque to be transmitted thereto.

9. A device for causing the matrix fibers in a living tissue sheet to be oriented in a desired direction, the device comprising a take-up unit for receiving and maintaining the living tissue sheet under tension, a tensor for inducing a controlled mechanical strain in the sheet along a predetermined direction while the sheet is being dispensed to the take-up unit, said take-up unit includes a winding mandrel keyed to an axle, wherein a thread extends along the winding mandrel, said thread is maintained under tension via two hooks associated with the axle, said thread is further selectively tensioned via a pair of moveable collars that are moveable along the length of the mandrel, the controlled mechanical strain causing the cells and the matrix fibers in the sheet to be aligned parallel to the predetermined direction.

10. A device as defined in claim 9, wherein said tensor is provided with a sheet engaging portion adapted to frictionally engage the living tissue sheet so as to apply a force of resistance on the sheet while the same is being dispensed to the take-up unit.

* * * * *